United States Patent [19]

Santalucia et al.

[11] Patent Number: 5,565,190
[45] Date of Patent: * Oct. 15, 1996

[54] DENTIFRICE COMPOSITIONS CONTAINING REACTIVE INGREDIENTS STABILIZED WITH ALKALI METAL COMPOUNDS

[75] Inventors: John Santalucia, New Brunswick; Richard J. Crawford, Asbury; David B. Viscio, Monmouth Junction; Nagaraj S. Dixit, Plainsboro; Michael A. Collins, Hazlet, all of N.J.

[73] Assignee: Colgate Palmolive Company, New York, N.Y.

[*] Notice: The portion of the term of this patent subsequent to Nov. 14, 2014, has been disclaimed.

[21] Appl. No.: 339,093

[22] Filed: Nov. 14, 1994

[51] Int. Cl.$^6$ ............................ A61K 7/16; A61K 7/20; A61K 33/40; A61K 39/10
[52] U.S. Cl. ............................ 424/53; 424/49
[58] Field of Search ........................ 424/49–58

[56] References Cited

U.S. PATENT DOCUMENTS

| | | | |
|---|---|---|---|
| 2,982,396 | 5/1961 | Shihadell | 206/47 |
| 3,747,804 | 7/1973 | Raaf et al. | 222/1 |
| 3,980,767 | 9/1976 | Chown et al. | 424/52 |
| 4,098,435 | 7/1978 | Weyn | 722/94 |
| 4,328,205 | 5/1982 | Taylor | 424/52 |
| 4,358,437 | 11/1982 | Duke | 424/49 |
| 4,405,599 | 9/1983 | Smigel | 424/53 |
| 4,487,757 | 12/1984 | Kiozpeuplou | 424/49 |
| 4,565,691 | 1/1986 | Jackson | 424/52 |
| 4,568,534 | 2/1986 | Stier et al. | 424/49 |
| 4,603,045 | 7/1986 | Smigel | 424/52 |
| 4,687,663 | 8/1987 | Schaefer | 424/52 |
| 4,814,160 | 3/1989 | Carter et al. | 424/49 |
| 4,837,008 | 6/1989 | Rudy et al. | 424/53 |
| 4,897,258 | 1/1990 | Rudy et al. | 424/53 |
| 4,971,782 | 11/1990 | Rudy et al. | 424/53 |
| 5,041,280 | 8/1991 | Smigel | 424/52 |
| 5,264,205 | 11/1993 | Kelly et al. | 424/53 |
| 5,324,505 | 6/1994 | Kornettka et al. | 424/49 |
| 5,372,803 | 12/1994 | Williams et al. | 424/53 |

*Primary Examiner*—Shep K. Rose
*Attorney, Agent, or Firm*—Paul Shapiro

[57] ABSTRACT

A dentifrice composition containing reactive ingredients such as peroxide and bicarbonate compounds which are stabilized to decomposition during storage by incorporating in dentifrice composition about 1.0 to about 5.0% by weight of an alkali metal compound.

4 Claims, No Drawings

DENTIFRICE COMPOSITIONS CONTAINING REACTIVE INGREDIENTS STABILIZED WITH ALKALI METAL COMPOUNDS

BACKGROUND OF THE INVENTION

1. Field of the Invention

The invention relates generally to a dentifrice composition containing reactive ingredients and more particularly to a dentifrice composition improved storage stability containing reactive peroxide and bicarbonate ingredients.

2. The Prior Art

It has been found to be very desirable to incorporate peroxide compounds in dentifrice compositions, the efficacy of peroxide compounds in oral hygiene having long been recognized. Such compounds have been proven effective in the treatment of gingivitis, periodontitis and in combating plaque. Additionally, peroxide compounds have been utilized for oral cosmetic purposes such as tooth whitening which results from bleaching and cleansing of tooth surfaces. A problem encountered with dentifrices formulated with peroxide compounds, is that the peroxide compounds tend to exhibit undesirable stability and decompose when subjected to a storage environment of abnormally high temperature, e.g., temperatures in excess of 100° F. This problem is exacerbated when peroxide compounds are utilized in combination with other reactive ingredients such as sodium bicarbonate. The tendency of the peroxide compounds to react with such other ingredients presents significant stability problems with respect to providing products which achieve adequate shelf life.

The instability during storage is due to the reactive ingredients having a tendency to react or decompose in the dentifrice vehicle when subjected to a storage environment of abnormally high temperatures. Due to such instability, the presence of the reactive ingredients causes gasing and bloating of the containers in which the dentifrice product is stored rendering the product unacceptable for consumer use.

Examples of prior art attempts at providing stable peroxide containing dentifrices in which a bicarbonate ingredient is also included are found in the disclosures of U.S. Pat. No. 4,971,782, U.S. Pat. No. 4,897,258 and U.S. Pat. No. 4,837,008.

U.S. Pat. No. 4,837,008 discloses an aqueous dentifrice containing a peroxide and/or bicarbonate ingredient in which the ingredients are provided with a barrier coating to prevent reaction of the ingredients. A disadvantage to such dentifrice is that release of the ingredients for cleaning effect during use is diminished by the presence of the barrier coating.

U.S. Pat. No. 4,897,258 discloses an anhydrous dentifrice containing calcium peroxide and sodium bicarbonate wherein the anhydrous state of the dentifrice prevents reaction between the ingredients. A disadvantage to such dentifrice is that in spite of the anhydrous state of the dentifrice, limited storage stability is experienced.

U.S. Pat. No. 4,971,782 discloses an anhydrous dentifrice containing peroxide and bicarbonate ingredients in which one of the ingredients is coated with a water dissolvable coating and a peroxide stabilizer is included in the dentifrice to further enhance storage stability. In spite of the presence of the stabilizer, the dentifrice remains deficient in storage stability required for commercial use.

Because of the storage stability problems with dentifrices containing reactive ingredients such as peroxides and bicarbonate compounds, dentifrices containing either the peroxide or bicarbonate compound are separately maintained before use. For example, U.S. Pat. No. 4,687,663 discloses placing each of a peroxide gel and bicarbonate paste into separate compartments of a single two-compartment container to avoid interaction between these ingredients before use. Such dual packaging devices are costly to manufacture and attempts at simultaneous even delivery of the two separate dentifrice components from the dual compartmented device is many times erratic.

There is therefore a need in the art for a dentifrice containing peroxide and other reactive ingredients such as bicarbonate salts which dentifrice remains stable during storage for extended periods of time and can be stored without provision for costly physical separation of components.

SUMMARY OF THE INVENTION

In accordance with the present invention, the stability of dentifrice compositions containing reactive ingredients such as peroxides and bicarbonate compounds which decomposes to produce gaseous products in storage at elevated temperatures is substantially improved by incorporating in the dentifrice an effective stabilizing amount of an alkali metal compound.

DESCRIPTION OF THE PREFERRED EMBODIMENTS

The vehicle used to prepare the stabilized dentifrice composition of the present invention is contains limited amounts of water and includes a suitable humectant which is a substantially anhydrous viscous material, such as glycerin, sorbitol, polyethylene glycol, or any suitable mixture thereof. A mixture of glycerin and a polyethylene glycol is preferred as the humectant in the practice of the present invention. Limited amounts of water may be included in the vehicle of the dentifrice components and preferably no more than about 9% by weight of the composition and most preferably about 5 to about 8% by weight water. When water is present in the dentifrice components in amounts in excess of about 9% by weight, the stability of the dentifrice components begins to be adversely affected.

The proportion of vehicle used to prepare the dentifrice composition of the present invention is generally within the range of about 40 to about 70% by weight of the paste or gel dentifrice component of this invention and preferably about 50 to about 65% by weight of the dentifrice component. Glycerin is present in the dentifrice vehicle of the present invention at a concentration of about 10 to about 60% by weight and preferably about 15 to about 40% by weight.

A surfactant is used in the preparation of dentifrice composition of the present invention to aid in prophylactic action and in the thorough dispersion of the dentifrice composition throughout the oral cavity when applied thereto as well as to improve the cosmetic acceptability and detersive and foaming properties of the dentifrice. Among the organic surfactants useful in the practice of the present invention are salts of the higher alkyl sulfates, such as sodium lauryl sulfate (SLS) or other suitable alkyl sulfate having 8 to 18 carbon atoms in the alkyl group; sodium lauryl sulfoacetate, salts of sulfonated monoglycerides of higher fatty acids, such as sodium coconut monoglyceride sulfonate or other suitable sulfonated monoglycerides of a fatty acids of 10 to 18 carbon atoms; salts of amides of higher fatty acid, e.g., 12 to 16 carbon atom acids, with lower aliphatic amino acids, such as sodium-N-methyl-N-palmitoyl tauride, sodium N-lauroyl-, N-myristoyl- and N-palmitoyl sarcosinates; salts of the esters of such fatty acids with isothionic acid or with glycerol monosulfate, such as the sodium salt of monosulfated monoglyceride of hydrogenated coconut oil fatty acids; salts of olefin sulfonates, e.g. alkene sulfonates or hydroxyalkene sulfonates or mixtures thereof having 12 to 16 carbon atoms in the carbon chain of the molecule; and soaps of higher fatty acids, such as those of 12 to 18 carbon atoms, e.g., coconut fatty acids. The cation of the salt may be sodium, potassium or mono-, di or triethanol amine.

The surfactant is included in the dentifrice vehicle of the present invention at a concentration of about 0.5; to about 3.0% by weight and preferably about 1.0 to about 2.0% by weight.

Polishing agents are incorporated in dentifrice composition of the present invention and preferred polishing agents are siliceous materials, such as silica, and will normally have a mean particle size up to about 10 microns and a very high surface area, e.g. in the range of 150–750 square meters/gram. A preferred silica is a precipitated amorphous hydrated silica, such as Sorbosil AC-35 marketed by Crosfield Chemicals, or Zeoclent 115 from J. M. Huber Company but other polishing agents may also be employed, including peroxide reactive polishing agents such as sodium bicarbonate, calcium carbonate, as well as sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, alumina trihydrate, aluminum silicate, zirconium silicate, calcined alumina and bentonite.

Bicarbonate compounds when included the dentifrice components of the present invention are present at a concentration of about 5 to about 20% by weight and preferably about 8 to about 15% by weight. The particle size of the bicarbonate compound can range from about 10 to about 300 microns although a particle size of 20–60 microns is preferred, the smaller particle size bicarbonate being more readily dispersed in the dentifrice vehicle.

The polishing agent is present in the dentifrice composition of the present invention at a concentration of about 10 to about 30% by weight and preferably about 5 to about 25% by weight.

Inorganic thickeners may be included in the dentifrices of the present invention and include fumed silicas such as Cab-o-sil available from Cabot Corporation, and thickening silias including those available from W. R. Grace designated Sylox 15.

Organic thickeners such as natural and synthetic gums and colloids may also be incorporated in the dentifrice composition of the present invention. particularly when water in amounts up to about 9% by weight are present in the dentifrice component. Examples of such thickeners include carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose.

The inorganic or organic thickener may be incorporated in the compositions of the present invention at a concentration of about 0.05 to about 2% by weight and preferably about 0.1 to about 1.5% by weight.

Peroxide compounds used as an ingredient in the dentifrice composition of the present invention are present in the dentifrice composition at a concentration of about 0.25 to about 5% by weight and preferably about 0.5 to about 2.0% by weight. Peroxide compounds suitable for use in the practice of the present invention include metal peroxides such as calcium peroxide, magnesium peroxide, and zinc peroxide.

To stabilize the dentifrice compositions of the present invention, a water soluble alkali metal compound which functions to inhibit the formation of undesirable gaseous products during storage is included in the dentifrice composition. Examples of such alkali metal compounds include alkali metal hydroxides, cabonates, sesquicarbonates, borates and silicates such as sodium hydroxide, potassium hydroxide, sodium carbonate, potassium carbonate, sodium borate, sodium sesquicarbonate and sodium silicate.

The water soluble alkali metal compound is incorporated in the composition of the present invention at concentrations in the range of about 0.05 to about 5.0% by weight and preferable about 0.1 to about 3.0% by weight. It has been determined that when sodium carbonate is used to stabilize the dentifrice compositions of the present invention that the maximum particle size of the salt is preferably less than 150 microns and most preferably less than 100 microns.

Fluorine-providing salts having anti-caries efficacy may also be incorporated in the dentifrice of the present invention and are characterized by their ability to release fluoride ions in water. It is preferable to employ a water-soluble salt fluoride providing about 10–2,000 ppm of fluoride ion, and preferably about 1000–1500 ppm of fluoride ion. Among these materials are water-soluble inorganic metal salts, for example, sodium fluoride, potassium fluoride, sodium monofluorophosphate and sodium fluorosilicate. Sodium fluoride and sodium monofluorophosphate are preferred fluorine-providing salts.

Salts having anti-tartar efficacy including water soluble salts such as dialkali or tetra-alkali metal pyrophosphate salts such as $Na_4P_2O_7$, (TSPP) $K_4P_2O_7$, $Na_2K_2P_2O_7$, $Na_2H_2P_2O_7$ and $K_2H_2P_2O_7$, long chain polyphosphates such as sodium hexametaphosphate and cyclic phosphates such as sodium trimetaphosphate as well as alkali metal tripolyphosphates such as sodium tripolyphosphate (STPP) add potassium tripolyphosphate may be incorporated in the dentifrice products of the present invention preferably at a concentration of about 0.5 to about 8.0% by weight.

Colorants such as pigments and dyes may be used in the practice of the present invention. Pigments include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C B&D #30 lake and FD&C # Yellow 15 lake. The pigments have a particle size in the range of 5–1000 microns, preferably 250–500 microns, and are present at a concentration of 0.5 to 3% by weight.

Dyes used in the practice of the present invention are generally food color additives presently certified under the Food Drug & Cosmetic Act for use in food and ingested drugs, including dyes such as FD&C Red No. 3 (sodium salt of tetraiodofluorescein), FD&C Yellow No. 5 (sodium salt of 4-p-sulfophenylazo-1-p-sulfophenyl- 5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)methylene}-[1-(N-ethyl-N-p-sulfobenzyl)-Δ-3,5-cyclohexadienimine], FD&C Blue No. 1 (disodium salt of dibenzyldiethyldiaminotriphenylcarbinol trisulfonic acid anhydrite), FD&C Blue No. 2(sodium salt of disulfonic acid of indigotin) and mixtures thereof in various proportions. The concentration of the dye for the most effective result in the present invention is present in the dentifrice composition in an amount from about 0.05 percent to about 10 percent by weight with respect to the weight of the total dentifrice component and preferably present from about 0.0005 percent to about 2 percent of the total weight of the component.

Any suitable flavoring or sweetening material may also be incorporated in the dentifrice composition of the present invention. Examples of suitable flavoring constituents are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, sodium cyclamate, perillartine, and sodium saccharin. Suitably, flavor and sweetening agents may together comprise from 0.01% to 5% or more of the preparations.

Various other materials may be incorporated into the dentifrice composition of this invention. Non-limiting examples thereof include preservatives, silicones and chlorophyll compounds, antibacterial agents such as chlorohexidene, halogenated diphenyl ethers such as Triclosan, desensitizing agents such as potassium nitrate and potassium citrate and mixtures thereof. These adjuvants are incorporated in the dentifrice composition in amounts which do not substantially adversely affect the properties and characteristics desired, and are selected and used in proper amounts, depending upon the particular type of dentifrice component involved.

To prepare the dentifrice composition of the present invention, the humectants e.g. glycerin, and polyethylene glycol ingredients and sweetner are dispersed in a conventional mixer until the mixture becomes a homogeneous gel phase. Into the gel phase are added a colorant and any tartar control agents such as TSPP or STPP or both and fluoride anti-caries agents such as sodium monofluorophosphate. These ingredients are mixed until a homogeneous phase is obtained. Thereafter the thickener, polishing agent, reactive ingredient such as peroxide and bicarbonate flavor compounds,. and surfactant ingredients are added and the ingredients mixed at high speed under vacuum of about 20–100 mm Hg. The resultant product is a homogeneous, semi-solid, extrudable paste product.

The following examples illustrate this invention further. All proportions and amounts therein and elsewhere in this specification are by weight unless otherwise indicated.

EXAMPLE I

To demonstrate the Stabilizing affect of $Na_2CO_3$ on the stability the compositions of the present invention during storage, a series of dentifrice compositions of the present invention designated Compositions A–G were prepared following the procedure previously described containing the ingredients listed in Table I below. For purposes of comparison, the procedure of Example 1 was repeated to prepare comparative compositions and H and I except that $Na_2CO_3$ was not included in the composition. The ingredients of compositions H and I are also listed in Table I below.

TABLE I

| Ingredients | A | B | C | D | E | F | G | H | I |
|---|---|---|---|---|---|---|---|---|---|
| Glycerin | 0.00 | 0.00 | 20.00 | 51.54 | 20.00 | 20.25 | 20.25 | 0.00 | 0.00 |
| PEG 400 | 51.54 | 50.54 | 31.54 | 0.00 | 29.54 | 30.29 | 30.29 | 53.54 | 52.54 |
| MFP | 0.76 | 0.76 | 0.76 | 0.76 | 0.76 | 0.76 | 0.76 | 0.76 | 0.76 |
| TSPP | 2.00 | 2.00 | 2.00 | 2.00 | 2.00 | 2.00 | 2.00 | 2.00 | 2.00 |
| TSPP | 3.00 | 3.00 | 3.00 | 3.00 | 3.00 | 3.00 | 3.00 | 3.00 | 3.00 |
| Saccharin | 0.50 | 0.50 | 0.50 | 0.50 | 0.50 | 0.50 | 0.50 | 0.50 | 0.50 |
| Zeodent 115 | 18.50 | 18.5 | 18.50 | 18.50 | 20.00 | 16.00 | 19.00 | 18.50 | 18.50 |
| Sylox 15 | 6.00 | 6.00 | 4.00 | 4.00 | 4.00 | 3.5 | 4.50 | 6.00 | 6.00 |
| $Na_2CO_3$ | 2.00 | 3.00 | 3.00 | 3.00 | 2.00 | 2.00 | 2.00 | 0.00 | 0.00 |
| Iota Gum | 0.00 | 0.00 | 1.00 | 1.00 | 0.00 | 0.00 | 0.00 | 0.00 | 1.00 |
| Xanthan Gum | 0.00 | 0.00 | 0.00 | 0.00 | 0.50 | 0.00 | 0.00 | 0.00 | 0.00 |
| Na Bicarb | 8.00 | 8.00 | 8.00 | 8.00 | 12.00 | 15.00 | 12.00 | 8.00 | 8.00 |
| Ca Peroxide | 2.00 | 2.00 | 2.00 | 2.00 | 1.00 | 2.00 | 1.00 | 2.00 | 2.00 |
| $TiO_2$ | 3.00 | 3.00 | 3.00 | 3.00 | 2.00 | 2.00 | 2.00 | 3.00 | 3.00 |
| SLS | 1.70 | 1.70 | 1.70 | 1.70 | 1.70 | 1.70 | 1.70 | 1.70 | 1.70 |
| Flavor | 1.00 | 1.00 | 1.00 | 1.00 | 1.00 | 1.00 | 1.00 | 1.00 | 1.00 |
| Total | 100.00 | 100.00 | 100.00 | 100.00 | 100.00 | 100.00 | 100.00 | 100.00 | 100.00 |

Individual plastic laminated tubes were filled with Compositions A–I, the tubes closed and then aged in heated air at 120° F. for 3 days. The aging results are summarized in Table II below.

TABLE II

| | Aging at 120° F. (3 days) | | | | | | | | |
|---|---|---|---|---|---|---|---|---|---|
| Composition | A | B | C | D | E | F | G | H | I |
| Gas Reaction Noted | No | No | No | No | No | No | No | Yes | Yes |
| Tube Bursting Noted | No | No | No | No | No | No | No | Yes | Yes |

EXAMPLE II

The procedure of Example I was repeated to prepare dentifrice compositions J–N with the exception that sodium hydroxide was substituted for sodium carbonate. The ingredients of the dentifrices are listed below in Table III. For purposes of comparison, the procedure of Example II was repeated to prepare comparative composition O which did not contain sodium hydroxide. The ingredients of composition O are also listed in Table III. The dentifrices were then tested for gas stability and the gas stability results are recorded in Tables IV below.

TABLE III

| Ingredients | Compositions | | | | | |
|---|---|---|---|---|---|---|
| | J | K | L | M | N | O |
| Glycerin | 20.00 | 20.00 | 52.04 | 42.04 | 32.04 | 20.00 |
| PEG 400 | 33.84 | 33.09 | 0.00 | 10.00 | 20.00 | 33.34 |
| MFP | 0.76 | 0.76 | 0.76 | 0.76 | 0.76 | 0.76 |
| TSPP | 2.00 | 2.00 | 2.00 | 2.00 | 2.00 | 2.00 |
| STPP | 3.00 | 3.00 | 3.00 | 3.00 | 3.00 | 3.00 |
| Saccharin | 0.50 | 0.50 | 0.50 | 0.50 | 0.50 | 0.50 |
| $TiO_2$ | 2.00 | 0.20 | 2.00 | 2.00 | 2.00 | 2.00 |
| Ca Peroxide | 1.00 | 1.00 | 1.00 | 1.00 | 1.00 | 1.00 |
| Zeodent 115 | 18.20 | 20.00 | 19.00 | 19.00 | 19.00 | 18.20 |
| Sylox 15 | 4.00 | 4.00 | 4.50 | 4.50 | 4.50 | 4.00 |
| Na Bicarb | 12.00 | 12.00 | 12.00 | 12.00 | 12.00 | 12.00 |
| Na Hydroxide (50%) | 0.50 | 0.25 | 0.50 | 0.50 | 0.50 | 0.00 |
| Iota | 0.00 | 0.00 | 0.00 | 1.00 | 1.00 | 0.00 |
| Xanthan Gum | 0.50 | 0.50 | 0.00 | 0.00 | 0.00 | 0.50 |
| SLS | 1.70 | 1.70 | 1.70 | 1.70 | 1.70 | 1.70 |
| Flavor | 1.00 | 1.00 | 1.00 | 1.00 | 1.00 | 1.00 |
| Total | 100.00 | 100.00 | 100.00 | 101.00 | 101.00 | 100.00 |

TABLE IV

| | Aging at 120° F. (3 days) | | | | | |
|---|---|---|---|---|---|---|
| Composition | J | K | L | M | N | O |
| Gas Reaction Noted | No | No | No | No | No | Yes |
| Tube Bursting Noted | No | No | No | No | No | Yes |

The results recorded in Tables II and IV above indicate that the presence of an alkali metal compound Such as sodium carbonate or sodium hydroxide in dentifrices containing reactive ingredients such as calcium peroxide and sodium bicarbonate (compositions A–H and J–N) substantially improve the storage stability of the dentifrice especially when compared to comparative compositions H, I and O in which gas reactions and tube bursting were noted.

What is claimed is:

1. An aqueous dentifrice composition for cleaning teeth containing reactive calcium peroxide and sodium bicarbonate ingredients which are stabilized to interaction or decomposition during storage, the composition being comprised of a vehicle containing about 4 to about 9% by weight water and an effective stabilizing amount of sodium hydroxide.

2. The composition of claim 1 wherein the vehicle contains about 4 to about 8% by weight water.

3. A method for improving the storage stability of aqueous dentifrice compositions containing reactive calcium peroxide and sodium bicarbonate ingredients which comprises preparing a vehicle for the dentifrice and then including in the vehicle an effective stabilizing amount of sodium hydroxide.

4. The method of claim 3 wherein the vehicle contains about 5 to about 8% by weight water.

* * * * *